(12) United States Patent
Thacker et al.

(10) Patent No.: US 9,895,538 B1
(45) Date of Patent: Feb. 20, 2018

(54) SYSTEMS AND METHODS FOR DEPLOYING PATIENT THERAPY DEVICES

(71) Applicant: Nevro Corporation, Menlo Park, CA (US)

(72) Inventors: James R. Thacker, Homer, AK (US); Andre B. Walker, Monte Sereno, CA (US); Jon Parker, San Jose, CA (US); Bradford Evan Gliner, Sammamish, WA (US); Heinz Moeri, Reinach (CH)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 14/161,592

(22) Filed: Jan. 22, 2014

Related U.S. Application Data

(60) Provisional application No. 61/755,286, filed on Jan. 22, 2013.

(51) Int. Cl.
*A61N 1/36* (2006.01)

(52) U.S. Cl.
CPC ..... *A61N 1/36071* (2013.01); *A61N 1/36132* (2013.01); *A61N 1/36157* (2013.01); *A61N 1/36171* (2013.01)

(58) Field of Classification Search
CPC .............. A61N 1/36071; A61N 1/3605; A61N 1/36164; A61N 1/36157; A61N 1/36171; A61N 1/36175; A61N 1/36132
See application file for complete search history.

(56) References Cited

U.S. PATENT DOCUMENTS

| | | |
|---|---|---|
| 4,019,519 A | 4/1977 | Geerling |
| 4,210,151 A | 7/1980 | Keller, Jr. |
| 4,257,429 A | 3/1981 | Dickhudt et al. |
| 4,340,063 A | 7/1982 | Maurer |
| 4,467,800 A | 8/1984 | Zytkovicz |
| 4,899,750 A | 2/1990 | Ekwall |

(Continued)

FOREIGN PATENT DOCUMENTS

| | | |
|---|---|---|
| JP | 08503648 | 4/1996 |
| JP | 20020527159 | 8/2002 |

(Continued)

OTHER PUBLICATIONS

Hayt et al., "Engine Circuit Analysis," McGraw-Hill Book Company, Fourth Edition, 1986, 18 pages.

(Continued)

*Primary Examiner* — George Evanisko
(74) *Attorney, Agent, or Firm* — Perkins Coie LLP

(57) ABSTRACT

Methods for identifying responders to paresthesia-free stimulation therapy, and associated systems are disclosed. A representative method comprises implanting a pair of spinal cord signal delivery devices and connecting an external signal generator thereto. A plurality of the electrical contacts are simultaneously activated with a high frequency signal without causing paresthesia in the patient, wherein the electrical contacts would cause paresthesia in the patient if activated with a low frequency signal. The high frequency signal is in a range of from about 3 kHz to about 20 kHz and an amplitude of less than 4 mA. If the patient responds favorably, a signal generator is implanted in the patient. A second high frequency signal is then applied to fewer than the plurality of electrical contacts.

20 Claims, 6 Drawing Sheets

(56) References Cited

U.S. PATENT DOCUMENTS

| | | |
|---|---|---|
| 5,016,635 A | 5/1991 | Graupe |
| 5,031,618 A | 7/1991 | Mullett |
| 5,063,929 A | 11/1991 | Bartelt et al. |
| 5,069,211 A | 12/1991 | Bartelt et al. |
| 5,143,081 A | 9/1992 | Young et al. |
| 5,159,926 A | 11/1992 | Ljungstroem |
| 5,184,617 A | 2/1993 | Harris et al. |
| 5,222,494 A | 6/1993 | Baker, Jr. |
| 5,223,226 A | 6/1993 | Wittmer et al. |
| 5,224,475 A | 7/1993 | Berg et al. |
| 5,342,409 A | 8/1994 | Mullett |
| 5,354,320 A | 10/1994 | Schaldach et al. |
| 5,423,329 A | 6/1995 | Ergas |
| 5,540,730 A | 7/1996 | Terry, Jr. et al. |
| 5,641,326 A | 6/1997 | Adams |
| 5,643,330 A | 7/1997 | Holsheimer et al. |
| 5,702,429 A | 12/1997 | King |
| 5,782,884 A | 7/1998 | Stotts et al. |
| 5,814,092 A | 9/1998 | King |
| 5,843,146 A | 12/1998 | Cross, Jr. |
| 5,891,179 A | 4/1999 | Er et al. |
| 5,913,882 A | 6/1999 | King |
| 5,938,690 A * | 8/1999 | Law .................. A61N 1/36071 607/46 |
| 6,052,624 A | 4/2000 | Mann |
| 6,155,267 A | 12/2000 | Nelson |
| 6,159,163 A | 12/2000 | Strauss et al. |
| 6,208,894 B1 | 3/2001 | Schulman et al. |
| 6,236,892 B1 | 5/2001 | Feler |
| 6,308,102 B1 | 10/2001 | Sieracki et al. |
| 6,319,241 B1 | 11/2001 | King et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,440,090 B1 | 8/2002 | Schallhorn |
| 6,461,357 B1 | 10/2002 | Sharkey et al. |
| 6,516,227 B1 | 2/2003 | Meadows et al. |
| 6,574,507 B1 | 6/2003 | Bonnet |
| 6,587,727 B2 | 7/2003 | Osorio et al. |
| 6,609,030 B1 | 8/2003 | Rezai et al. |
| 6,622,048 B1 | 9/2003 | Mann |
| 6,659,968 B1 | 12/2003 | McClure |
| 6,671,556 B2 | 12/2003 | Osorio et al. |
| 6,740,072 B2 | 5/2004 | Starkweather et al. |
| 6,803,102 B1 | 10/2004 | Talley et al. |
| 6,873,872 B2 | 3/2005 | Gluckman et al. |
| 6,895,280 B2 * | 5/2005 | Meadows ............ A61N 1/0553 607/2 |
| 6,909,917 B2 * | 6/2005 | Woods ............... A61N 1/37247 607/148 |
| 6,920,357 B2 | 7/2005 | Osorio et al. |
| 6,947,792 B2 | 9/2005 | Ben-Haim et al. |
| 6,978,171 B2 | 12/2005 | Goetz et al. |
| 6,993,384 B2 | 1/2006 | Bradley et al. |
| 7,010,345 B2 | 3/2006 | Hill et al. |
| 7,020,523 B1 | 3/2006 | Lu et al. |
| 7,024,246 B2 | 4/2006 | Acosta et al. |
| 7,024,247 B2 | 4/2006 | Gliner et al. |
| 7,050,856 B2 | 5/2006 | Stypulkowski |
| 7,110,821 B1 | 9/2006 | Ross |
| 7,123,967 B2 | 10/2006 | Weinberg |
| 7,127,296 B2 | 10/2006 | Bradley |
| 7,142,923 B2 | 11/2006 | North et al. |
| 7,174,215 B2 | 2/2007 | Bradley |
| 7,184,837 B2 | 2/2007 | Goetz |
| 7,191,012 B2 | 3/2007 | Boveja et al. |
| 7,206,632 B2 | 4/2007 | King |
| 7,239,920 B1 | 7/2007 | Thacker et al. |
| 7,239,926 B2 | 7/2007 | Goetz |
| 7,242,984 B2 | 7/2007 | DiLorenzo |
| 7,252,090 B2 | 8/2007 | Goetz |
| 7,263,402 B2 | 8/2007 | Thacker et al. |
| 7,266,412 B2 | 9/2007 | Stypulkowski |
| 7,286,878 B2 | 10/2007 | Stypulkowski |
| 7,289,851 B2 | 10/2007 | Gunderson et al. |
| 7,295,876 B1 | 11/2007 | Erickson |
| 7,317,948 B1 | 1/2008 | King et al. |
| 7,343,200 B2 | 3/2008 | Litvak et al. |
| 7,349,739 B2 | 3/2008 | Harry et al. |
| 7,403,821 B2 | 7/2008 | Haugland et al. |
| 7,406,351 B2 | 7/2008 | Wesselink |
| 7,414,534 B1 | 8/2008 | Kroll et al. |
| 7,444,181 B2 | 10/2008 | Shi et al. |
| 7,447,545 B2 | 11/2008 | Heruth et al. |
| 7,450,992 B1 | 11/2008 | Cameron |
| 7,463,927 B1 | 12/2008 | Chaouat |
| 7,483,747 B2 | 1/2009 | Gliner et al. |
| 7,489,970 B2 | 2/2009 | Lee et al. |
| 7,555,346 B1 | 6/2009 | Woods et al. |
| 7,571,001 B2 | 8/2009 | Thacker et al. |
| 7,603,175 B2 | 10/2009 | Voelkel |
| 7,617,002 B2 | 11/2009 | Goetz |
| 7,634,315 B2 | 12/2009 | Cholette |
| 7,647,101 B2 | 1/2010 | Libbus et al. |
| 7,657,317 B2 | 2/2010 | Thacker et al. |
| 7,660,628 B2 | 2/2010 | Libbus et al. |
| 7,706,889 B2 | 4/2010 | Gerber et al. |
| 7,747,330 B2 | 6/2010 | Nolan et al. |
| 7,783,349 B2 | 8/2010 | Libbus et al. |
| 7,799,021 B2 | 9/2010 | Leung et al. |
| 7,801,601 B2 | 9/2010 | Maschino et al. |
| 7,801,619 B2 | 9/2010 | Gerber et al. |
| 7,801,621 B1 | 9/2010 | Thacker et al. |
| 7,819,909 B2 | 10/2010 | Goetz et al. |
| 7,831,305 B2 | 11/2010 | Gliner |
| 7,831,307 B1 | 11/2010 | Moffitt |
| 7,853,322 B2 | 12/2010 | Bourget et al. |
| 7,853,323 B2 | 12/2010 | Goetz |
| 7,872,884 B2 | 1/2011 | Parramon et al. |
| 7,873,418 B2 | 1/2011 | Stypulkowski |
| 7,881,805 B2 | 2/2011 | Bradley et al. |
| 7,945,330 B2 | 5/2011 | Gliner et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,966,073 B2 | 6/2011 | Pless et al. |
| 8,016,776 B2 | 9/2011 | Bourget et al. |
| 8,095,220 B2 | 1/2012 | Lee et al. |
| 8,116,878 B1 | 2/2012 | Palmer |
| 8,121,703 B1 | 2/2012 | Palmer |
| 8,170,675 B2 | 5/2012 | Alataris et al. |
| 8,175,719 B2 | 5/2012 | Shi et al. |
| 8,311,639 B2 | 11/2012 | Parker et al. |
| 8,355,797 B2 | 1/2013 | Caparso et al. |
| 8,457,759 B2 | 6/2013 | Parker et al. |
| 8,498,710 B2 | 7/2013 | Walker et al. |
| 8,626,312 B2 | 1/2014 | King et al. |
| 8,676,331 B2 | 3/2014 | Parker |
| 8,712,533 B2 | 4/2014 | Alataris et al. |
| 8,712,535 B2 | 4/2014 | Walker et al. |
| 9,295,840 B1 | 3/2016 | Thacker et al. |
| 2002/0068930 A1 | 6/2002 | Tasto et al. |
| 2002/0107553 A1 | 8/2002 | Hill et al. |
| 2002/0165586 A1 | 11/2002 | Hill et al. |
| 2003/0004549 A1 | 1/2003 | Hill et al. |
| 2003/0093134 A1 | 5/2003 | Bradley |
| 2003/0100931 A1 | 5/2003 | Mullett |
| 2003/0135248 A1 | 7/2003 | Stypulkowski |
| 2003/0153959 A1 | 8/2003 | Thacker et al. |
| 2003/0195582 A1 | 10/2003 | Mann |
| 2003/0212445 A1 | 11/2003 | Weinberg |
| 2004/0015202 A1 | 1/2004 | Chandler et al. |
| 2004/0116978 A1 | 6/2004 | Bradley |
| 2004/0138516 A1 | 7/2004 | Osorio et al. |
| 2004/0167584 A1 | 8/2004 | Carroll et al. |
| 2004/0215286 A1 | 10/2004 | Stypulkowski |
| 2005/0033381 A1 | 2/2005 | Carter et al. |
| 2005/0060001 A1 | 3/2005 | Singhal et al. |
| 2005/0060007 A1 | 3/2005 | Goetz |
| 2005/0209645 A1 | 9/2005 | Heruth et al. |
| 2005/0209655 A1 | 9/2005 | Bradley et al. |
| 2005/0245987 A1 | 11/2005 | Woods et al. |
| 2006/0111754 A1 | 5/2006 | Rezai et al. |
| 2006/0116742 A1 | 6/2006 | De Ridder |

(56) References Cited

U.S. PATENT DOCUMENTS

| | | |
|---|---|---|
| 2006/0135998 A1 | 6/2006 | Libbus et al. |
| 2006/0161236 A1 | 7/2006 | King |
| 2006/0195159 A1 | 8/2006 | Bradley et al. |
| 2006/0235472 A1 | 10/2006 | Goetz et al. |
| 2006/0247732 A1 | 11/2006 | Wesselink |
| 2006/0253174 A1 | 11/2006 | King |
| 2006/0253182 A1 | 11/2006 | King |
| 2006/0259099 A1 | 11/2006 | Goetz et al. |
| 2006/0293720 A1 | 12/2006 | DiLorenzo |
| 2007/0039625 A1 | 2/2007 | Heruth et al. |
| 2007/0073357 A1 | 3/2007 | Rooney et al. |
| 2007/0100378 A1 | 5/2007 | Maschino |
| 2007/0129774 A1 | 6/2007 | Bourget et al. |
| 2007/0135868 A1 | 6/2007 | Shi et al. |
| 2007/0150029 A1 | 6/2007 | Bourget et al. |
| 2007/0156207 A1 | 7/2007 | Kothandaraman et al. |
| 2007/0179579 A1 | 8/2007 | Feler et al. |
| 2007/0208394 A1 | 9/2007 | King et al. |
| 2007/0213773 A1 | 9/2007 | Hill et al. |
| 2007/0213789 A1 | 9/2007 | Nolan et al. |
| 2007/0245318 A1* | 10/2007 | Goetz ............... A61N 1/36071 717/135 |
| 2007/0249968 A1 | 10/2007 | Miesel et al. |
| 2007/0255118 A1 | 11/2007 | Miesel et al. |
| 2007/0265679 A1 | 11/2007 | Bradley et al. |
| 2007/0265681 A1 | 11/2007 | Gerber et al. |
| 2007/0276450 A1 | 11/2007 | Meadows et al. |
| 2007/0276453 A1 | 11/2007 | Hill et al. |
| 2008/0015657 A1 | 1/2008 | Haefner |
| 2008/0046036 A1 | 2/2008 | King et al. |
| 2008/0046052 A1 | 2/2008 | Werder et al. |
| 2008/0051839 A1 | 2/2008 | Libbus et al. |
| 2008/0064980 A1 | 3/2008 | Lee et al. |
| 2008/0071325 A1 | 3/2008 | Bradley |
| 2008/0103570 A1 | 5/2008 | Gerber |
| 2008/0109050 A1 | 5/2008 | John |
| 2008/0140150 A1 | 6/2008 | Zhou et al. |
| 2008/0154340 A1 | 6/2008 | Goetz et al. |
| 2008/0183256 A1 | 7/2008 | Keacher |
| 2008/0188909 A1 | 8/2008 | Bradley |
| 2008/0215118 A1 | 9/2008 | Goetz et al. |
| 2008/0243196 A1 | 10/2008 | Libbus et al. |
| 2008/0281381 A1 | 11/2008 | Gerber et al. |
| 2008/0319511 A1 | 12/2008 | Pless |
| 2009/0005833 A1 | 1/2009 | Cameron et al. |
| 2009/0018617 A1 | 1/2009 | Skelton et al. |
| 2009/0030476 A1 | 1/2009 | Hargrove |
| 2009/0054946 A1 | 2/2009 | Sommer et al. |
| 2009/0112281 A1 | 4/2009 | Miyazawa et al. |
| 2009/0112282 A1 | 4/2009 | Kast et al. |
| 2009/0125079 A1 | 5/2009 | Armstrong et al. |
| 2009/0149917 A1* | 6/2009 | Whitehurst ........ A61N 1/36017 607/59 |
| 2009/0204173 A1 | 8/2009 | Fang et al. |
| 2009/0264956 A1 | 10/2009 | Rise et al. |
| 2009/0264957 A1 | 10/2009 | Giftakis et al. |
| 2009/0264967 A1 | 10/2009 | Giftakis et al. |
| 2009/0281594 A1 | 11/2009 | King et al. |
| 2009/0281595 A1 | 11/2009 | King et al. |
| 2009/0281596 A1 | 11/2009 | King et al. |
| 2009/0281599 A1 | 11/2009 | Thacker et al. |
| 2009/0306740 A1 | 12/2009 | Heruth et al. |
| 2009/0306746 A1 | 12/2009 | Blischak |
| 2009/0326608 A1 | 12/2009 | Huynh et al. |
| 2010/0010432 A1 | 1/2010 | Skelton |
| 2010/0010566 A1 | 1/2010 | Thacker et al. |
| 2010/0049280 A1 | 2/2010 | Goetz |
| 2010/0057162 A1* | 3/2010 | Moffitt ............... A61N 1/0551 607/46 |
| 2010/0069993 A1* | 3/2010 | Greenspan ......... A61N 1/0534 607/46 |
| 2010/0121408 A1 | 5/2010 | Imran et al. |
| 2010/0121409 A1* | 5/2010 | Kothandaraman ........................ A61N 1/37247 607/46 |
| 2010/0125314 A1 | 5/2010 | Bradley et al. |
| 2010/0131034 A1 | 5/2010 | Gliner et al. |
| 2010/0137944 A1 | 6/2010 | Zhu |
| 2010/0185256 A1 | 7/2010 | Hulvershorn |
| 2010/0211135 A1 | 8/2010 | Caparso et al. |
| 2010/0228325 A1 | 9/2010 | Moffitt et al. |
| 2010/0234912 A1 | 9/2010 | Ternes et al. |
| 2010/0274312 A1 | 10/2010 | Alataris et al. |
| 2010/0274314 A1 | 10/2010 | Alataris et al. |
| 2010/0274317 A1* | 10/2010 | Parker ............... A61N 1/36071 607/46 |
| 2010/0274320 A1 | 10/2010 | Torgerson |
| 2010/0274336 A1 | 10/2010 | Nguyen-Stella et al. |
| 2010/0305631 A1 | 12/2010 | Bradley et al. |
| 2010/0305660 A1 | 12/2010 | Hegi et al. |
| 2010/0312319 A1 | 12/2010 | Barker |
| 2011/0009927 A1 | 1/2011 | Parker et al. |
| 2011/0022141 A1 | 1/2011 | Chen et al. |
| 2011/0029040 A1 | 2/2011 | Walker et al. |
| 2011/0040348 A1 | 2/2011 | Wacnik et al. |
| 2011/0040351 A1 | 2/2011 | Butson et al. |
| 2011/0046697 A1 | 2/2011 | Gerber et al. |
| 2011/0054565 A1 | 3/2011 | Wacnik et al. |
| 2011/0071593 A1 | 3/2011 | Parker et al. |
| 2011/0087309 A1 | 4/2011 | Stypulkowski |
| 2011/0093051 A1 | 4/2011 | Davis et al. |
| 2011/0118661 A1 | 5/2011 | Pless et al. |
| 2011/0184488 A1* | 7/2011 | De Ridder ......... A61N 1/36071 607/46 |
| 2012/0083857 A1 | 4/2012 | Bradley et al. |
| 2012/0116476 A1 | 5/2012 | Kothandaraman |
| 2012/0130448 A1 | 5/2012 | Woods et al. |
| 2012/0172946 A1 | 7/2012 | Alataris et al. |
| 2012/0253422 A1 | 10/2012 | Thacker et al. |
| 2012/0265268 A1 | 10/2012 | Blum et al. |
| 2012/0265271 A1 | 10/2012 | Goetz |
| 2013/0023950 A1 | 1/2013 | Gauthier |
| 2013/0060302 A1 | 3/2013 | Polefko et al. |
| 2013/0066411 A1 | 3/2013 | Thacker et al. |
| 2013/0116754 A1 | 5/2013 | Sharma et al. |
| 2013/0261694 A1 | 10/2013 | Caparso et al. |
| 2013/0310892 A1 | 11/2013 | Parker et al. |
| 2014/0081349 A1* | 3/2014 | Lee .................... A61N 1/0551 607/46 |
| 2014/0330338 A1 | 11/2014 | Walker et al. |
| 2015/0217113 A1 | 8/2015 | Walker et al. |

FOREIGN PATENT DOCUMENTS

| | | |
|---|---|---|
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-2006119046 A1 | 11/2006 |
| WO | WO-2007149018 A1 | 12/2007 |
| WO | WO-2008142402 A1 | 11/2008 |

OTHER PUBLICATIONS

Keuchmann C et al., "853 Could Automatic Position Adaptive Stimulation be Useful in Spinal Cord Stimulation," Abstract, Medtronic, Inc., undated, 1 page.

U.S. Appl. No. 14/161,152, filed Jan. 22, 2014, Thacker et al.

U.S. Appl. No. 14/161,554, filed Jan. 22, 2014, Thacker et al.

U.S. Appl. No. 14/161,512, filed Jan. 22, 2014, Thacker.

* cited by examiner

SYSTEMS AND METHODS FOR DEPLOYING PATIENT THERAPY DEVICES

CROSS-REFERENCE TO RELATED APPLICATIONS

The present application claims the benefit of U.S. Provisional Application No. 61/755,286, filed Jan. 22, 2013, the disclosure of which is hereby incorporated by reference in its entirety. The present application is related to concurrently filed, applications identified by the disclosures of which are hereby incorporated by reference in their entireties. To the extent the forgoing materials and/or any other materials incorporated herein by reference conflict with the present disclosure, the present disclosure controls.

TECHNICAL FIELD

The present disclosure is directed generally to implantable neurological stimulation systems. More specifically, the disclosure is directed to methods for deploying patient therapy systems, such as spinal cord stimulation systems that do not use paresthesia to mask or cover a patient's sensation of pain.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In conventional SCS, the patient must first undergo a test (or "trial") period to determine if they are responsive to the therapy before a permanent system is implanted. Responders are identified by meticulously programming multiple programs into an "external" patient-worn trial stimulator system, and instructing the patient to choose the most beneficial program for pain relief. Each of these multiple programs corresponds to stimulating a combination of two or more electrodes out of a total available set of 16 or more electrodes. Because paresthesia over large areas can result in discomfort for most patients, only a few electrodes are activated at a time in each program, to minimize the uncomfortable side effects for the patient. Also, amplitude changes are small and controlled in order to avoid shocking the patient. Typically, this trial testing is performed in and/or outside a clinic under the supervision of a trained practitioner.

In contrast to conventional SCS, a form of "high frequency" SCS has been developed that uses high frequency electrical pulses delivered to the spinal cord to treat the patient's sensation of pain without generating paresthesia or otherwise using paresthesia to mask the patient's sensation of pain. Thus, conventional deployment methods, which rely on paresthesia for feedback, may not be adequate for deploying high frequency SCS systems. Accordingly, there is a need for methods of deploying high frequency SCS systems that account for paresthesia-free therapy.

SUMMARY

Disclosed herein are patient therapy systems, including high frequency spinal cord stimulation systems, methods for deploying patient therapy systems, and methods for identifying patient responders to a paresthesia-free spinal stimulation therapy. The disclosed embodiments can provide simplified procedures for initially determining if a patient is a responder and subsequently selecting and configuring therapy electrodes. These procedures can significantly reduce the service burden on practitioners who deploy and administer SCS therapy to patients.

In a representative embodiment, the method comprises implanting in a patient a pair of spinal cord signal delivery devices, each having at least eight electrical contacts. An external signal generator is connected to the spinal cord signal delivery devices. The method further comprises simultaneously activating a plurality of the electrical contacts with a high frequency signal without causing paresthesia in the patient while delivering therapy, wherein the plurality of electrical contacts would cause paresthesia in the patient if activated with a low frequency signal. In a particular embodiment, the high frequency signal is in a range of from about 1.5 kHz to about 100 kHz, for example, and an amplitude of less than 20 mA, for example. If the patient responds favorably to the simultaneous activation of the plurality of electrical contacts, a signal generator is implanted in the patient. After implanting the signal generator, a second high frequency signal is applied to fewer than the plurality of electrical contacts via the implanted signal generator.

DETAILED DESCRIPTION

Figure 1:
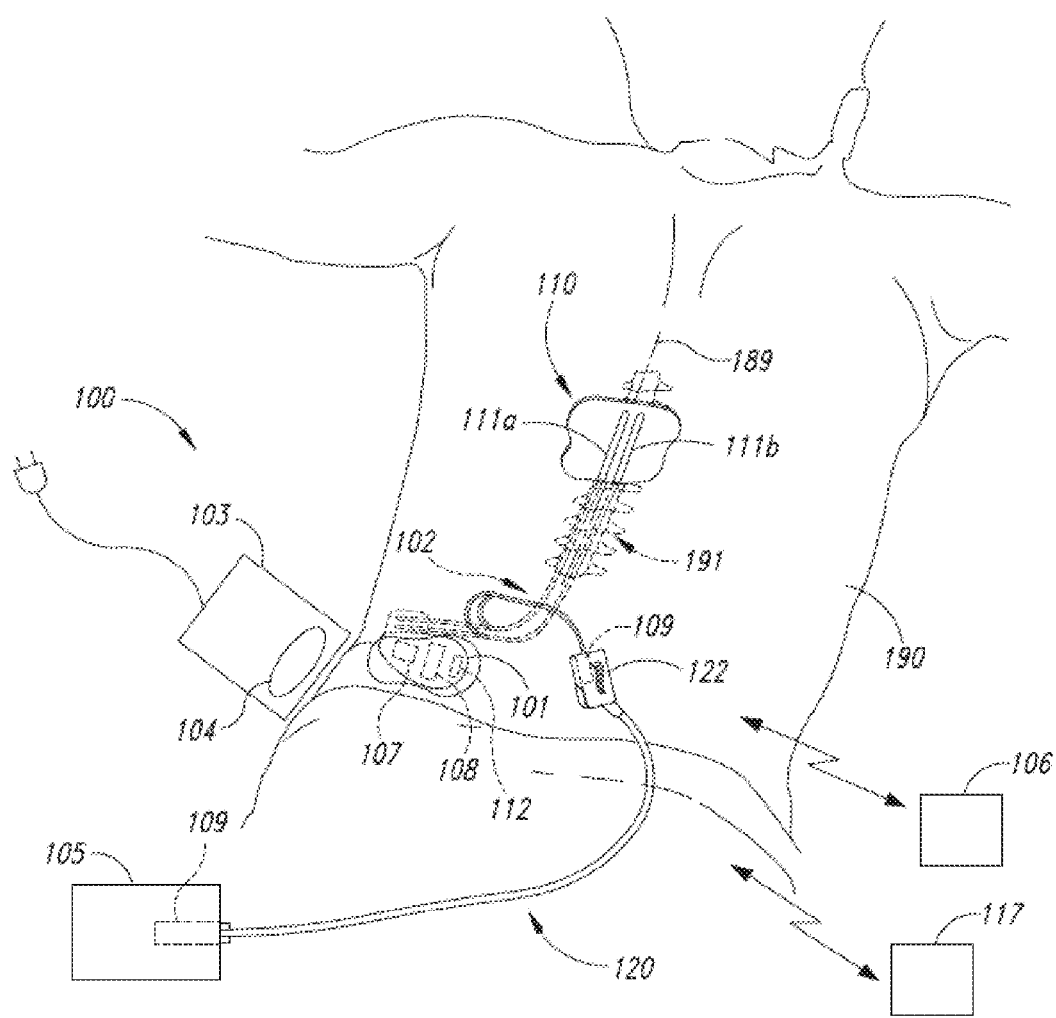
FIG. 1 is a partially schematic illustration of an implantable spinal cord stimulation system positioned at the spine to deliver therapeutic signals in accordance with several embodiments of the present disclosure.

The present technology is directed generally to deploying patient therapy systems, such as spinal cord stimulation (SCS) systems. For example, in one embodiment, the present technology is employed in SCS systems that provide pain relief without generating paresthesia, to identify early on those patients who respond favorably to the system. The technology can include delivering the therapy from a plurality of simultaneously activated electrodes while power is provided by an external signal generator, and then implanting a signal generator in the patient if they respond favorably. With the signal generator implanted, the number of active electrodes is reduced, e.g., to the minimum number necessary to achieve a target level of pain relief (or other therapeutic outcome) so as to reduce the power required by the implanted signal generator. This in turn can increase the length of time the implanted stimulator can operate without recharging.

In one embodiment, the systems and methods disclosed herein are applicable to "high frequency" paresthesia-free SCS systems. Such SCS systems, for example, inhibit, reduce, and/or eliminate pain via waveforms with high frequency elements or components (e.g., portions having high fundamental frequencies), generally with reduced or eliminated side effects, and associated methods. Such side effects can include unwanted motor stimulation or blocking, unwanted pain or discomfort, unwanted paresthesia, and/or interference with sensory functions other than the targeted pain. In a representative embodiment, a patient may receive high frequency therapeutic signals with at least a portion of the therapy signal at a frequency of from about 1.5 kHz to about 100 kHz, or from about 2.5 kHz to about 100 kHz, or from about 1.5 kHz to about 50 kHz, or from about 3 kHz to about 20 kHz, or from about 3 kHz to about 50 kHz, or from about 5 kHz to about 15 kHz, or at frequencies of about 8 kHz, 9 kHz, or 10 kHz. These frequencies are significantly higher than the frequencies associated with standard conventional "low frequency" SCS, which are generally below 1,200 Hz, and more commonly below 100 Hz. Accordingly, stimulation at these and other representative frequencies (e.g., from about 1.5 kHz to about 100 kHz) is occasionally referred to herein as high frequency modulation. As will be discussed below, alternative embodiments are directed to paresthesia-free SCS systems and therapies, in general, regardless of frequency.

The disclosed embodiments can provide simplified procedures for initially determining if a patient is a responder and subsequently selecting and configuring therapy electrodes. As used herein, the term responder refers generally to a patient who responds favorably to a particular therapeutic technique and/or system. Specific details of certain embodiments of the disclosure are described below with reference to methods for stimulating one or more target neural populations (e.g., nerves) or sites of a patient, and associated implantable structures for providing the stimulation. Although selected embodiments are described below with reference to stimulating the dorsal column, dorsal horn, dorsal root, dorsal root entry zone, and/or other particular regions of the spinal column to control pain, the stimulation may in some instances be directed to other neurological structures and/or target neural populations of the spinal cord and/or other neurological tissues. Some embodiments can have configurations, components or procedures different than those described in this section, and other embodiments may eliminate particular components or procedures. Accordingly, the disclosure may encompass other embodiments with additional elements and/or steps and may include other embodiments without several of the features or steps shown and described below with reference to FIGS. 1-6.

In general terms, aspects of many of the following embodiments are directed to simplifying the determination of whether a patient is responsive to the therapeutic effects of paresthesia-free SCS therapies, thereby allowing permanent implantation of a signal generator in less time than is required for conventional procedures. As such, it is expected that the techniques described below with reference to FIGS. 1-6 can provide paresthesia-free SCS therapy deployment procedures that are more efficient, in terms of time and/or cost, than existing deployment procedures associated with conventional, paresthesia-based SCS therapies. It is also expected that the described techniques can reduce the risk of infection associated with existing extended trial periods.

As described above, a form of high frequency SCS therapy has been developed that does not cause paresthesia. Further, it has been found that there may be a delay before high frequency SCS provides a patient with effective pain relief. Therefore, with high frequency SCS, the patient and practitioner may not immediately know if a patient is a responder to the therapy. This situation does not exist with conventional SCS because paresthesia generated by conventional SCS results in an immediate or near immediate response in the patients, although the optimal settings may take some time to determine. In conventional deployment techniques, various pairs of contacts are tested in sequence to determine the best pain relief. Testing each pair of contacts in high frequency SCS entails waiting a delay period (usually 1-2 days) and repeating the process until pain relief is achieved. Consequently, conventional trial period processes can take weeks (depending on the number of pairs tested) when used in the context of some high frequency therapy techniques. The methods disclosed herein can provide an advantage in deploying high frequency SCS in that a plurality of contacts are simultaneously activated, thereby limiting the number of times the delay period is encountered during the trial period.

FIG. 1 schematically illustrates a representative patient therapy system 100 for providing relief from chronic pain and/or other conditions, arranged relative to the general anatomy of a patient's spinal column 191. The system 100 can include a signal generator 101 (e.g., a pulse generator), which may be implanted subcutaneously within a patient 190 and coupled to one or more signal delivery elements or devices 110. The signal delivery elements or devices 110 may be implanted within a patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms lead and lead body include any of a number of suitable substrates and/or support members that carry devices for providing therapy signals to the patient 190. For example, the lead or leads 111 can include one or more electrodes or electrical contacts 115 (see FIGS. 3A-6) that direct electrical signals into the patient's tissue, such as to provide for patient pain relief. In other embodiments, the signal delivery elements 110 can include structures other than a lead body (e.g., a paddle) that also direct electrical signals and/or other types of signals to the patient 190.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing stimulation signals, providing guidance information for positioning the signal delivery devices 110, and/or executing other associated functions can be performed by computer-executable instructions contained by computer-readable media located at the pulse generator 101 and/or other system components. The signal generator 101 can include multiple portions, elements, and/or subsystems (e.g., for directing signals in accordance with multiple signal delivery parameters), carried in a single housing, as shown in FIG. 1, or in multiple housings. In any of these embodiments, the signal generator 101 (and/or an external trial modulator 105, described further below) can automatically execute one or more programs. For example, during a trial period, the external trial stimulator 105 can automatically apply a signal to all or a significant subset (e.g., 50% or 75%) of the electrical contacts available for treating the patient.

The signal generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1 for purposes of illustration) that are carried by the signal generator 101 and/or distributed outside the signal generator 101 (e.g., at other patient locations) while still communicating with the signal generator 101. The sensors 112 can provide inputs that depend on or reflect patient state (e.g., patient position, patient posture and/or patient activity level), and/or inputs that are patient-independent (e.g., time). Still further details are included in co-pending U.S. application Ser. No. 12/703,683, filed on Feb. 10, 2010 and incorporated herein by reference in its entirety.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use. In one embodiment, external power source 103 can by-pass an implanted signal generator and generate a therapy signal directly at the signal delivery device 110 (or via signal relay components).

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial portion of the procedure, prior to implanting the signal generator 101. For example, a practitioner (e.g., a physician and/or a company representative) can use the trial modulator 105 to vary the stimulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The pulse generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. Receiving elements 109 can be at least generally similar in structure and function to those described in U.S. patent application Ser. No. 13/291, 985, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated herein by reference in its entirety.

After the signal delivery elements 110 are implanted, the patient 190 can receive therapy via signals generated by the trial modulator 105, generally for a limited period of time. Traditionally, the patient 190 receives such therapy for one week. However, with the deployment methods disclosed herein, this time may be reduced, e.g., to about 1-2 days. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with parameters selected based on the experience gained during the trial period. Optionally, the practitioner can also replace the signal delivery elements 110. Once the implantable signal generator 101 has been positioned within the patient 190, the signal delivery parameters provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude.

In any of the foregoing embodiments, the parameters in accordance with which the signal generator 101 provides signals, can be adjusted during portions of the therapy regimen. For example, the frequency, amplitude, pulse width and/or signal delivery location can be adjusted in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Certain aspects of the foregoing systems and methods may be simplified or eliminated in particular embodiments of the present disclosure. Further aspects of these and other expected beneficial results are detailed in co-pending U.S. application Ser. No. 12/765,810, filed on Apr. 22, 2010; U.S. patent application Ser. No. 12/765,747, filed Apr. 22, 2010; and U.S. patent application Ser. No. 12/264,836, filed Nov. 4, 2008, all of which are incorporated herein by reference in their entireties.

A form of high frequency SCS therapy has recently been determined to deliver therapy without generating paresthesia or unwanted pain or other sensory or motor effects to achieve effective therapy. (Such high frequency SCS therapy is described in more detail in the above-incorporated U.S. application Ser. No. 12/765,810 (published as U.S. Patent Application Publication No. 2010-0274314).) Aspects of the present technology are directed to techniques and systems for detecting whether a patient is a responder, despite the absence of paresthesia. For example, in accordance with embodiments of the present technology, the practitioner can simultaneously apply signals to all or a significant subset of the electrical contacts 115 of the signal delivery device(s) 110 without causing undesired side effects. Using this technique, the practitioner can quickly determine if the patient 190 is a responder to the therapy or not. This is unlike conventional SCS techniques, which typically require an iterative electrode-by-electrode trial and error process to determine whether the patient is a responder (a procedure commonly referred to as "paresthesia mapping" in conventional SCS therapy). If all or a significant subset of electrodes were activated simultaneously using conventional SCS, the patient would typically be overstimulated, causing immense pain and/or other undesirable side effects. In addition, conventional SCS techniques require close supervision in a clinic to perform the necessary electrode-by-electrode trial and error process.

Activating all or many of the electrodes simultaneously can also consume a significant amount of power. However, during the trial phase, the power source for the trial is not implanted but is carried externally by the patient in an external trial stimulator. Accordingly, the battery used during the trial phase can be much larger than an implanted power supply, so as to provide adequate power to the larger number of active electrodes.

Figure 2:
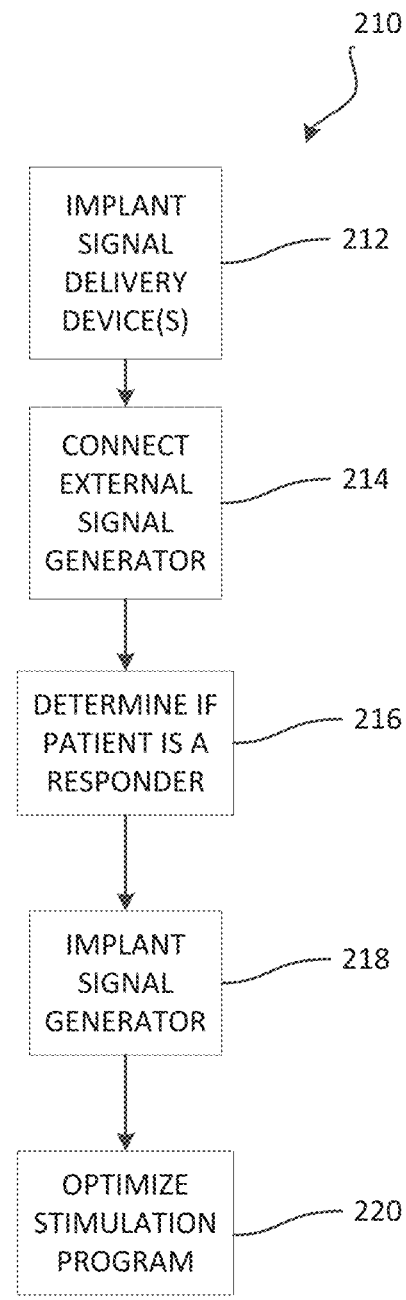
FIG. 2 is a flow diagram illustrating features of the disclosed methods.

FIG. 2 is a flow diagram illustrating methods for deploying paresthesia-free SCS therapy in accordance with particular embodiments of the present disclosure. Method 210 includes implanting signal delivery devices 110 (e.g., a lead, paddle or other suitable device) at the patient's spinal cord region (block 212). The spinal cord region can include epidural and/or subdural regions, at or off the midline, including the dorsal root, dorsal root entry zone and the dorsal root ganglia. The particular location within the spinal cord region can depend upon the patient and/or the particular embodiment of the present technology. For example, one device may be implanted on one side of the spinal cord midline 189 (FIG. 1), and a second device may be implanted on the other side of the spinal cord midline 189. In another example, one device may be implanted in the epidural space and another device may be implanted subcutaneously. The leads 111 (FIG. 1) may be positioned just off the spinal cord midline 189 (e.g., about 1 mm. offset) in opposing lateral directions so that the two leads 111 are spaced apart from each other by about 2 mm. The leads 111 may be implanted at a vertebral level ranging from, for example, about T8 to about T11 as shown in FIGS. 3A-6 to address lower back pain and/or leg pain, and can be implanted at other vertebral levels to address other patient indications.

The method 210 further includes connecting an external signal generator 105 to the implanted signal delivery devices 110 (block 214). The electrical contacts 115 are activated with (e.g., have applied to them) high frequency (or other paresthesia-free) therapy signals in accordance with one or more of several embodiments, described more fully below, in order to determine whether or not the patient is a responder to high frequency (or other paresthesia-free) SCS therapy (block 216). If the patient is a responder to high frequency SCS (or other paresthesia-free) therapy (e.g., if the patient shows improvement in a condition, and/or the likelihood of such an improvement), a signal generator is implanted in the patient (block 218). After the patient has been identified as a responder and the signal generator is implanted in the patient, further programming optimization (block 220) may be performed to select the program that optimally (or in an improved manner) enables pain relief with the least (or a reduced) number of electrical contacts, thereby lengthening device battery life in the permanent implant. Such a process for optimizing or otherwise improving the therapy is preferably completed after permanent implant, when there is more time available to determine the target (e.g., optimal) program. The process can be performed automatically and/or with input from the patient and/or practitioner.

In a representative embodiment, programming optimization can include activating all of the electrodes or a suitable subset of electrodes and using a binary search routine to remove electrodes or pairs of electrodes from the set of activated electrodes to identify the minimum number of electrodes that provide effective pain relief. In some embodiments, programming optimization can be performed during the trial phase using a trial stimulator that is capable of providing adequate power to a larger number of active electrodes. In other embodiments, programming optimization can be performed after the permanent signal generator is implanted; however, the implant battery may require more frequent charging.

In light of the foregoing, it should be appreciated that the disclosed methods and systems provide an efficient procedure for determining if a patient responds to paresthesia-free SCS therapy, before (a) implanting a permanent signal generator and (b) closing the incision that is required when using an external trial stimulator. Using these methods may effectively determine if a patient is a responder in significantly less time as compared to using conventional SCS trial procedures for paresthesia-free SCS therapy. Accordingly, advantages of the foregoing technique include, amongst other things, (1) saving patient, physician, and practitioner time; (2) identifying the most-effective therapy for the patient as soon as possible; and (3) reducing the time during which the patient has a lead extending outside the body, and therefore, the likelihood for infection. Another advantage of the foregoing technique is that the programs can be tested over a period of time outside the clinic as the patient goes about his/her normal activities. It has been determined that paresthesia-free SCS therapies may not be immediately effective in relieving pain and can take at least approximately 20 minutes or greater (e.g., 48 hours) to produce pain relief. Therefore, the disclosed methods have the additional advantage of allowing extended testing outside the clinic to help ensure that each configuration is adequately tested.

FIGS. 3A-6 illustrate electrical contact activation configurations according to several representative embodiments, which may be used to determine whether the patient is a responder (block 216 of FIG. 2). In each of the embodiments illustrated in FIGS. 3A-6, two signal delivery devices 110 are positioned along vertebral levels T8-T11. One of the signal delivery devices, a first lead 111a, is positioned over T8-T10. The second signal delivery device, a second lead 111b, overlaps the first lead 111a and is positioned over T9-T11. This overlapping configuration provides for redundant vertebral coverage in an area that has a high probability of therapeutic success. In addition, the overlap can account for movement of the leads 111 along the spinal column 191. The first lead 111a includes electrical contacts 115 designated 1-8 and the second lead 111b includes electrical contacts 115 designated 9-16. In other embodiments, other signal delivery devices with more or fewer electrical contacts may be used. In still further embodiments, the practitioner uses only a single signal delivery device to address the target neural populations. A single device can address neural populations at multiple vertebral levels and/or in a contralateral and/or bilateral manner, as discussed further in issued U.S. Pat. No. 8,170, 675, incorporated herein by reference in its entirety.

Figure 3A:
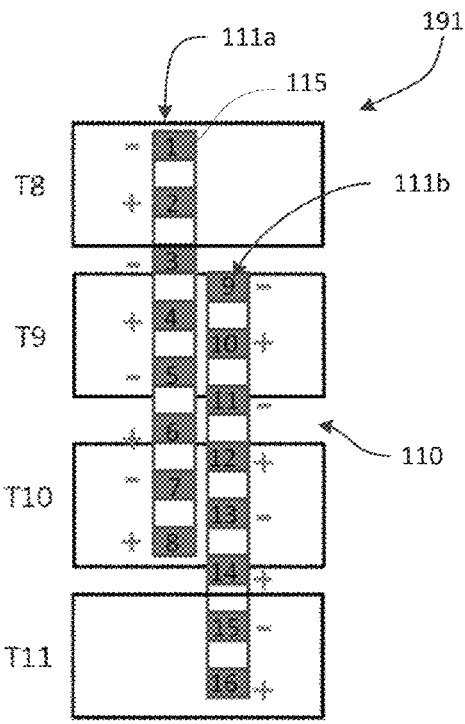
FIG. 3A is a schematic representation of several vertebrae and a plurality of simultaneously active electrical contacts according to a representative embodiment.

FIG. 3A illustrates an electrical contact activation configuration according to a representative embodiment for which a plurality of the electrical contacts 115 are activated simultaneously with alternating anodes (+) and cathodes (−), as shown. In this example, all of the electrical contacts 1-16 are simultaneously activated with a high frequency therapy signal. In some cases, however, certain contacts may not be activated. For example, contacts that are overlapping or relatively close together may not provide effective therapy while drawing too much current from other contacts. For example, in FIG. 3C, overlapping contacts 9-13 are not active, but contacts 14-16 are active. In this embodiment, linear alternating polarity is maintained from the first lead 111a (contacts 1-8) to the second lead 111b (contact 14 (−), contact 15 (+), and contact 16 (−)). In this manner, interference between the two leads is avoided yet the full available range of vertebral levels is covered. In some cases, the signal delivery devices 110 may be implanted such that they do not overlap to avoid shorting between contacts, which might otherwise prevent a location from being properly tested. In some cases, certain contacts may be affected by variability in the patient's tissue (e.g., fat deposits) causing the contact to have a high impedance.

Figure 3B:
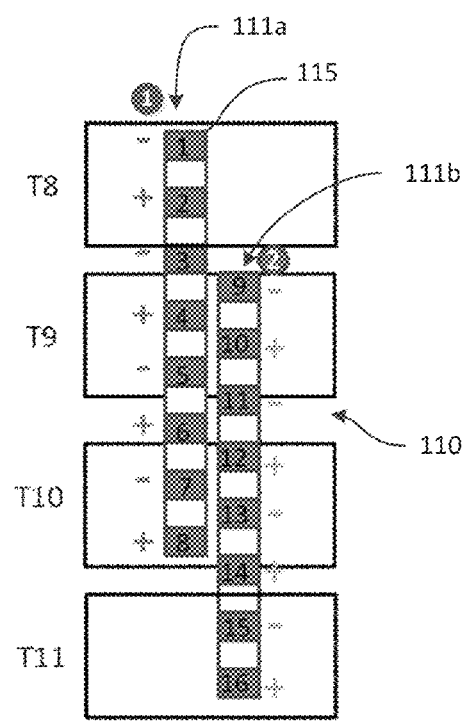
FIG. 3B is a schematic representation of several vertebrae and a plurality of electrical contacts that are activated in an alternating manner according to another representative embodiment.
Figure 3C:
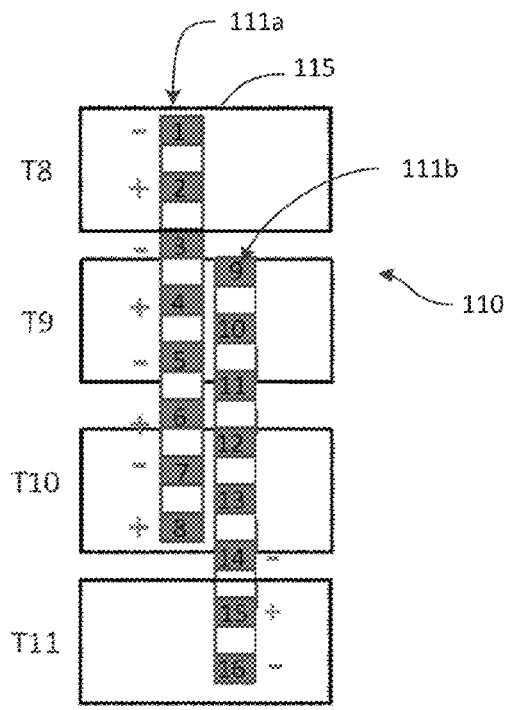
FIG. 3C is a schematic representation of several vertebrae and a plurality of simultaneously active electrical contacts according to still another representative embodiment.

FIG. 3B illustrates an electrical contact activation configuration according to another representative embodiment. In this case, the signal delivery devices 110 are located along the spine in a manner similar to that described above with respect to FIG. 3A. However, in this case the electrical contacts 115 are activated in an alternating fashion between the electrical contacts 115 of the first lead 111a and the second lead 111b. Thus, the active contacts alternate between a first set of contacts 1-8 (indicated by circled numeral 1) on the first lead 111a and a second set of contacts 9-16 (indicated by circled numeral 2) on the second lead 111b. Therefore, only half (i.e., 50%) of the total number of available electrical contacts 115 across both signal delivery devices are simultaneously activated. The entire number of available electrical contacts 115 on one or the other of the signal delivery devices are simultaneously activated in an alternating manner.

Figure 4A:
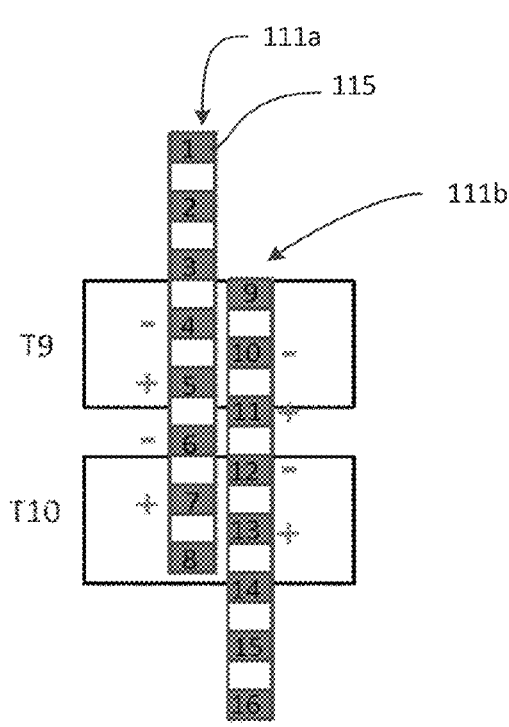
FIG. 4A is a schematic representation of two vertebrae and a plurality of simultaneously active electrical contacts according to yet another representative embodiment.
Figure 4B:
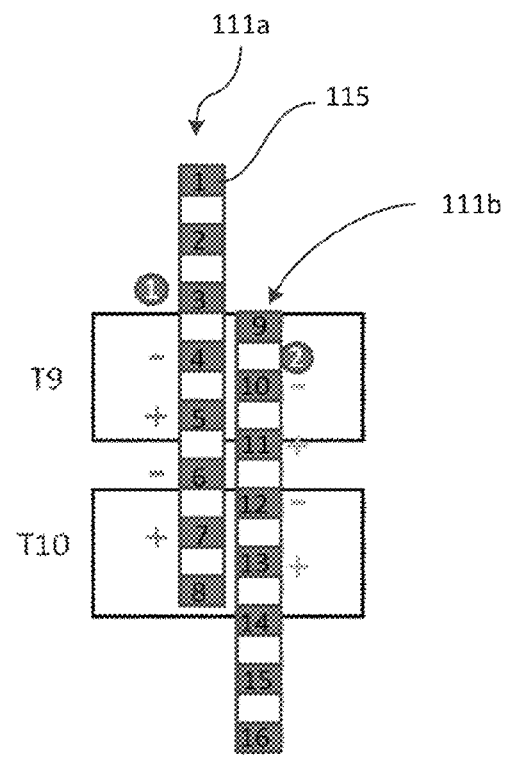
FIG. 4B is a schematic representation of two vertebrae and a plurality of electrical contacts that are activated in an alternating manner according to another representative embodiment.

FIGS. 4A and 4B illustrate further representative embodiments of electrical contact activation configurations. The leads 111a, 111b are located along the spine in a manner similar to that described above with respect to FIGS. 3A and 3B. In these embodiments, the high frequency stimulation is directed to T9 and T10. In FIG. 4A, for example, electrical contacts 4-7 and 10-13, which are located over T9 and T10, are simultaneously activated. FIG. 4B illustrates a process for alternating between a first set of contacts on the first lead 111a and a second set of electrical contacts on the second lead 111b. In this case, the first set includes contacts 4-7 (indicated by circled numeral 1) and the second set includes contacts 10-13 (indicated by circled numeral 2). Therefore, each set includes 25% of the total number of available electrical contacts 115 across both signal delivery devices.

Figure 5A:
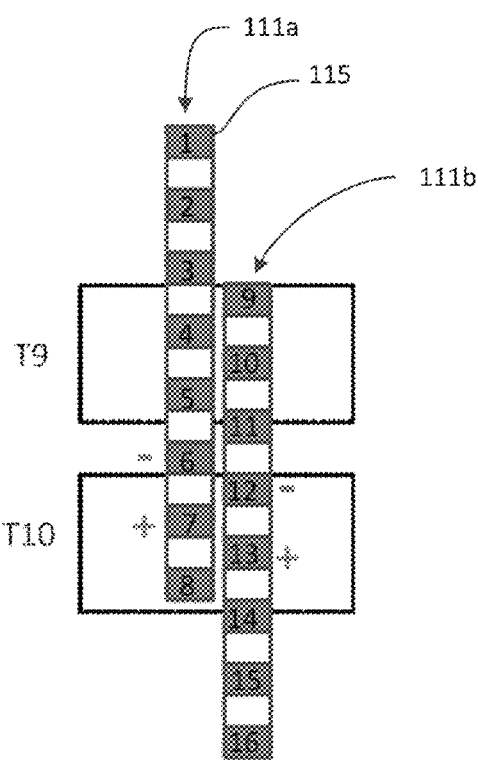
FIG. 5A is a schematic representation of two vertebrae and a plurality of simultaneously active electrical contacts according to still another representative embodiment.
Figure 5B:
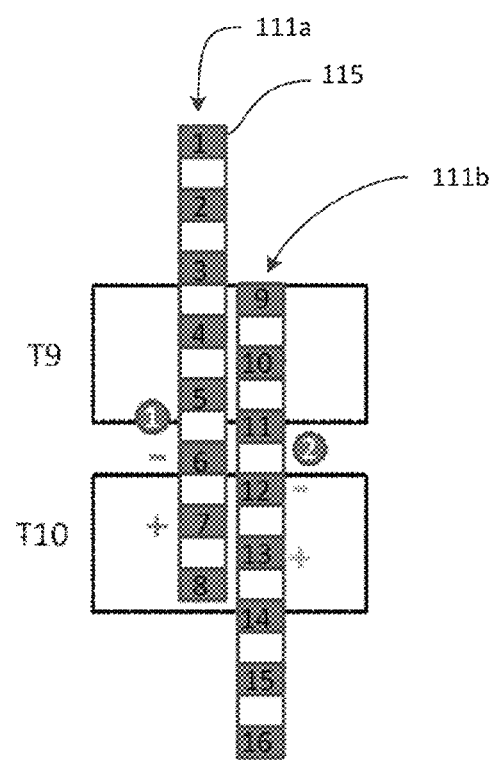
FIG. 5B is a schematic representation of two vertebrae and a plurality of electrical contacts that are activated in an alternating manner according to yet another representative embodiment.
Figure 6:
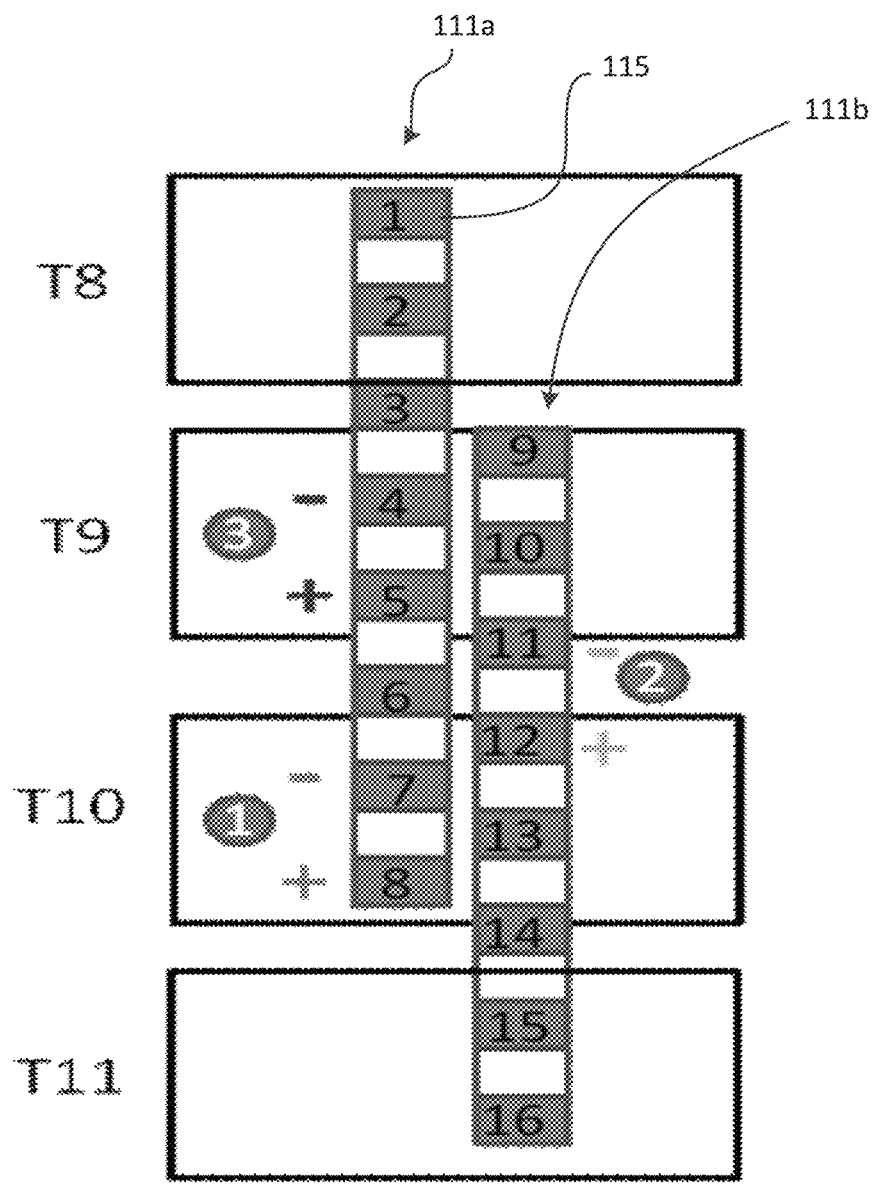
FIG. 6 is a schematic representation of several vertebrae and a plurality of electrical contacts that are activated in an alternating manner according to a further representative embodiment.

It should be appreciated that other combinations of electrical contacts may be selected as the plurality of electrical contacts that are simultaneously activated with a high frequency signal to determine if a patient is a responder or not. FIG. 5A illustrates an embodiment for which T10 is targeted for therapy by simultaneously activating contacts 6, 7, 12, and 13, as shown. Thus, 25% of the available contacts are simultaneously activated. FIG. 5B illustrates alternating between a first set of contacts, including contacts 6 and 7 (indicated by circled numeral 1), and a second set of contacts including contacts 12 and 13 (indicated by circled numeral 2). It should also be appreciated that alternating activation may alternate between more than two sets of contacts. For example, as shown in FIG. 6, simultaneous activation can alternate between three sets of contacts (indicated by circled numerals 1, 2, and 3). In this example, the first set includes contacts 7 and 8, the second set includes contacts 11 and 12, and the third set includes contacts 4 and 5. In this case, the sets of contacts are activated moving cephalad (i.e., toward the patient's head); however, multiple sets may be activated in any suitable order, such as caudal, away from the patient's head. Other patterns of alternating sets of contacts may be used depending on the number of sets and the area being targeted.

While the various embodiments show adjacent electrical contacts as alternating between anode (+) and cathode (−), other suitable combinations of anodes and cathodes are used in other embodiments. For example, all of the electrical contacts on a signal delivery device may be set as cathodes except for one anode. As another example, all of the electrical contacts on a signal delivery device may be set as cathodes with a skin surface patch or the implanted signal generator, for example, acting as the anode. Thus, the electrode configuration can be any suitable combination of cathodes and anodes that use all or a subset of all available electrodes on the signal delivery devices.

It should be understood that the above disclosed electrical contact activation configurations are not expected to be effective with conventional, paresthesia-based SCS stimulation. That is, these configurations would either cause the patient discomfort or fail to provide pain relief if activated with paresthesia-producing signals. For example, conventional low frequency SCS therapy includes stimulation at a frequency of less than 1,500 Hz (e.g., 40-80 Hz) and a pulse width of 100 μsec-1 ms. The amplitude of the signal (e.g., the current amplitude) is typically varied from about 3 mA to about 10 mA. One of ordinary skill in the art will recognize that conventional, paresthesia-producing SCS over the electrical contact activation configurations described above would be expected to cause extreme discomfort in the patient.

In another representative embodiment, a single program can cyclically activate multiple subsets of available electrodes in sequence. For example, in a particular embodiment, the high frequency SCS system can have 16 electrodes which are divided into three groups or subsets, with two electrodes in each subset. Each subset can be stimulated in sequence for a selected period of time before repeating the sequence. Thus, the program continuously cycles between the three subsets. This is distinct from the case in which all three subsets of electrodes are activated simultaneously. In some embodiments, each of the three subsets are activated at a duty cycle of 33.3% (i.e., ⅓ of the total cycle time), such that one of the three subsets is active at any given time. In other words, there is not a time delay between the activation of subsequent subsets. In other embodiments, each subset can be activated for less than ⅓ of the total cycle time, such that there is a time delay between the activation of subsequent subsets.

Driver circuits for the signal delivery devices may be voltage or current output sources. A particular embodiment includes at least one sink or source for two or more electrical contacts. In a further embodiment, one current sink and/or current source are provided for each electrical contact. In this configuration, it is possible to individually control the current delivered to each electrical contact. For example, for an 8 electrical contact signal delivery device, each output circuit controls one bipole. The output circuit includes a sink and a source, and the current is controlled within the compliance voltage of the output circuit.

In another embodiment, a lesser number of output circuits are switched between a relatively greater number of electrodes. For example, an 8 electrical contact signal delivery device may be activated by 1-4 output circuits that apply therapy using bipoles covering the entire length of the device. In this case, the output circuits are switched between the electrical contacts to allow spatial separation of the stimulation on different bipoles. Alternatively, the electrical contacts may be ganged together in a single electrode combination when the impedances are within a similar range. Thus, the cathodes tied to a single sink output circuit are in a similar impedance range and the anodes ganged together are in a different impedance range. In this embodiment, the electrodes can be removed from the ganged arrangement if the impedance associated with those electrodes is or becomes out of range.

Electrodes may be ganged together based on paresthesia threshold and impedance. If an electrode pair has a much lower paresthesia threshold but the same impedance as another pair, it may not be desirable to couple the two to a single current source. In cases for which the paresthesia threshold corresponds to an effective high frequency therapy amplitude window, (but is offset upwardly from the therapy amplitude window) the paresthesia threshold can be used to set up pairs of electrodes that will work together with a single current source, and then time multiplex between the pairs (e.g., with different amplitudes in at least some embodiments). For example, the patient can receive paresthesia-inducing signals to determine a threshold value, and electrodes with similar threshold values can then be grouped together, with the understanding that a positive correlation exists between the paresthesia threshold and a therapy threshold or other parameter.

In another embodiment, the contacts may be grouped according to impedance, with all of the contacts in the group falling within a particular impedance range. Each group can be operated by a current source (e.g., a current source dedicated to that group). The impedance of each contact is monitored, and if a particular contact's impedance varies from the range, it can be dropped from the group. Alternatively, the contact may be switched to a different group having a matching impedance range. In a further embodiment, out of range contacts are not switched or dropped until changes in current used to compensate for changes in impedance reach a selected threshold level, at which point the contact with the highest impedance is dropped or switched to another group.

In a particular embodiment, cross-correlation of the voltage gradients between electrodes can be used to automate avoiding laterally adjacent contacts. One contact can be activated as a cathode and each remaining contact can be activated as an anode in order to compare the voltage between different anodes. For example, contact 1 (e.g., FIG. 6) can be activated as a cathode and the voltage at contacts 4 and 9 can be compared in order to determine the proximity of the contacts.

Certain of the foregoing embodiments can produce one or more of a variety of advantages, for the patient and/or the practitioner, when compared with conventional SCS therapies. Some of these benefits were described above. For example, one advantage includes simplifying the determination of whether a patient is responsive to the therapeutic effects of high frequency SCS systems, thereby allowing permanent implantation of a signal generator in less time than is required when using conventional procedures. As such, high frequency SCS system deployment can be more efficient, in terms of time and burden on patients and/or practitioners.

Normally, activating all or many of the electrodes simultaneously can consume a significant amount of power. This is not typically a problem with the battery capacity of a trial modulator. However, with an implanted signal generator it is desirable to limit the number of contacts that are activated in order to conserve battery life. Yet another feature of embodiments of the foregoing therapy is that a large area of high frequency stimulation therapy coverage may be achieved with acceptable power consumption levels by activating the contacts at relatively low duty cycles when compared to conventional SCS therapy. Therefore, in accordance with embodiments of the present technology, effective high frequency SCS therapy may be achieved with an implanted signal generator without the need for programming optimization to select the least number of electrical contacts. Instead, many contacts can be activated at a low duty cycle (e.g., less than about 50%, less than about 30%, less than about 20%, less than about 17%, less than about 14%, or about 10% or less) and in a time multiplexed manner to cover a large therapy area with low power consumption.

Disclosed herein are patient therapy systems, including high frequency spinal cord stimulation systems and methods for deploying patient therapy systems. In a representative embodiment, the method includes implanting in a patient at least one spinal cord signal delivery device having multiple electrical contacts. In a representative embodiment, the spinal cord signal delivery device includes at least eight electrical contacts. An external signal generator is connected to at least one spinal cord signal delivery device and a plurality of the electrical contacts are simultaneously activated with a high frequency signal without causing discomfort in the patient while delivering therapy. The plurality of electrical contacts would cause discomfort in the patient if activated with a low frequency signal at the same amplitude. If the patient responds favorably to simultaneous activation of the plurality of electrical contacts, a signal generator is implanted in the patient.

In another embodiment, a method for deploying a patient therapy system includes implanting in a patient at least one spinal cord signal delivery device, having at least eight electrical contacts. An external signal generator is connected to at least one spinal cord signal delivery device and a plurality of the electrical contacts are simultaneously activated with a high frequency signal, wherein the plurality of electrical contacts includes at least 50% of the electrical contacts. If the patient responds favorably to simultaneous activation of the plurality of electrical contacts, a signal generator is implanted in the patient.

In a further representative embodiment, a method for deploying a patient therapy system includes implanting in a patient at least one spinal cord signal delivery device having multiple electrical contacts. An external signal generator is connected to at least one spinal cord signal delivery device. It is determined whether the patient responds favorably to a first high frequency stimulation signal by applying the signal to a first plurality of the electrical contacts. The first plurality of contacts may include contacts expected not to produce a therapeutic effect. If the patient responds favorably, a signal generator is implanted into the patient and a second high frequency stimulation signal is applied to a second plurality of electrical contacts fewer than the first plurality of electrical contacts via the implanted signal generator.

In yet another embodiment, a method for deploying a patient therapy system includes implanting in a patient at least one spinal cord signal delivery device, having multiple electrical contacts. An external signal generator is connected to the at least one spinal cord signal delivery device and a plurality of the electrical contacts are simultaneously activated with a high frequency signal without causing paresthesia in the patient while delivering therapy, wherein the plurality of electrical contacts would cause paresthesia in the patient if activated with a low frequency signal at the same amplitude. If the patient responds favorably to simultaneous activation of the plurality of electrical contacts, a signal generator is implanted in the patient.

In another representative embodiment, a method for deploying a patient therapy system includes implanting in a patient at least one spinal cord signal delivery device, having at least eight electrical contacts. A signal generator is connected to the at least one spinal cord signal delivery device. An impedance of individual contacts is monitored and individual contacts are grouped into a first group and a second group based on the impedance of the individual contacts. The first group of contacts is then simultaneously activated with a high frequency signal using a first current source. In a particular embodiment, the method further includes simultaneously activating the second group of contacts with a high frequency signal using a second current source. The method may further include removing a selected contact from the first group if the selected contact's impedance is outside a selected range. In another embodiment, the selected contact is included in the second group. In a still further representative embodiment, the method includes monitoring a compensation current needed to compensate for changes in an overall impedance of the first group, identifying a high impedance contact from the first group, and removing the high impedance contact from the first group if the compensation current exceeds a threshold current level.

Also disclosed herein are systems and devices for implementing the disclosed methods for deploying a high frequency SCS system. In a representative embodiment, a patient therapy system includes at least one patient implantable spinal cord signal delivery device having at least eight electrical contacts and an external trial modulator. The trial modulator has at least one mode (e.g., an automatically executed mode) in which a high frequency stimulation signal is simultaneously applied to a plurality of the electrical contacts, wherein the plurality of the electrical contacts is at least 50% of the electrical contacts. In a further representative embodiment, a patient therapy device includes a signal generator connectable to at least one spinal cord signal delivery device having at least eight electrical contacts. The signal generator is operative, in a trial phase, to apply a high frequency stimulation signal simultaneously to a first plurality of the electrical contacts. The first plurality of the electrical contacts is greater in number than a second plurality of electrical contacts used in a therapy phase.

In certain aspects of the disclosed technology, the plurality of electrical contacts can include at least 25% of the electrical contacts. In further embodiments, the plurality of contacts can include at least half, or 50%, of the electrical contacts. In still further embodiments, the plurality of electrical contacts can include at least 75% of the available electrical contacts. In yet further embodiments, the plurality of electrical contacts can include all of the electrical contacts. Two spinal cord signal delivery devices, each having multiple (e.g., eight) electrical contacts, may be implanted in the patient. Thus, the patient therapy system may include 16 electrical contacts. The method may further include after implanting the signal generator, applying a second high frequency signal to fewer than the plurality of electrical contacts via the implanted signal generator.

In certain embodiments, the amplitude of the therapy signal can range from about 0.1 mA to about 20 mA, or from about 0.5 mA to about 10 mA, or about 0.5 mA to about 4 mA, or from about 0.5 mA to about 2.5 mA. In other embodiments, the amplitude of the therapy signal can be less than about 2.5 mA or less than about 4 mA. In general, the higher amplitudes can be associated with multiple, simultaneously activated bipoles, as higher currents may be required to drive multiple bipoles (assuming a single current source). The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, filed Nov. 4, 2008, previously incorporated herein by reference.

In certain embodiments, the pulse width (e.g., for just the cathodic phase of the pulses) of the therapy signal can vary from about 10 microseconds to about 333 microseconds. In further particular embodiments, the pulse width can range from about 25 microseconds to about 166 microseconds, or from about 30 microseconds to about 100 microseconds, or from about 30 microseconds to about 35 microseconds.

In some embodiments, applying a short pulse width waveform via the signal generator and the signal delivery device is effective in providing pain relief without generating paresthesia. Many such examples are described herein in the context of high frequency signals (e.g., signals with a frequency of 1.5 kHz to 100 kHz). In other embodiments, the signals can have short pulse widths, at high or low frequencies. In particular examples, the signal (or at least a portion of the signal) can have pulses with pulse widths ranging from about 10-50 microseconds, or from about 20-40 microseconds, or from about 25-35 microseconds, or from about 30-35 microseconds, or about 30 microseconds.

In other embodiments, longer on and off time periods are effective. For example, in a representative embodiment, the paresthesia-free modulation signal can be on for approximately 10 seconds and off for approximately 120 seconds or on for approximately 20 seconds and off for approximately 120 seconds. In another embodiment, the paresthesia-free modulation signal can be on for 10-20 seconds and off for 60-120 seconds. The amplitude of the waveform (e.g., the amplitudes of the individual pulses) can be from about 0.5-20 mA, or from about 2-18 mA, or from about 5-15 mA, or from about 7-10 mA, or about 0.5-7 mA. Meanwhile, the frequency of the therapy signal (or at least a portion of the signal) can be at or below 1.5 kHz, e.g., from about 2 Hz to about 1.5 kHz, or from about 500 Hz to about 1.5 kHz, or from about 700 Hz to about 1.5 kHz, or from about 1 kHz to about 1.5 kHz, or about 1.2 kHz. In one representative example, the therapy signal includes a frequency of 1,200 Hz, a pulse width of 30 microseconds, and an amplitude that provides pain relief without generating paresthesia (generally between 0.5-20 mA).

In any of the foregoing embodiments, aspects of the therapy provided to the patient may be varied within or outside the representative parameters described above, while still obtaining beneficial results for patients suffering from chronic pain and/or other indications. For example, the location of the signal delivery device (and in particular, the signal delivery device electrical contacts or electrodes) can be varied over the significant lateral and/or axial ranges.

The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in particular embodiments, the signal amplitude refers to the electrical current level, e.g., for current-controlled systems. In other embodiments, the signal amplitude can refer to the electrical voltage level, e.g., for voltage-controlled systems. In cases for which the signal generator includes a constant voltage arrangement rather than a constant current arrangement, the current values described above may be replaced with corresponding voltage values.

Many embodiments of the technology described above may take the form of computer-executable instructions, including routines executed by a programmable computer. Those skilled in the relevant art will appreciate that the technology can be practiced on computer systems other than those shown and described below. The technology can be embodied in a special-purpose computer or data processor that is specifically programmed, configured or constructed to perform one or more of the computer-executable instructions described below. Accordingly, the term "computer" or "controller" as generally used herein refers to any suitable data processor and can include Internet appliances and hand-held devices (including palm-top computers, wearable computers, cellular or mobile phones, multi-processor systems, processor-based or programmable consumer electronics, network computers, mini computers and the like). Information handled by these computers can be presented at any suitable display medium, including a CRT display or LCD.

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. In particular embodiments, data structures and transmissions of data particular to aspects of the technology are also encompassed within the scope of the technology.

From the foregoing, it will be appreciated that specific embodiments of the disclosed technology have been described herein for purposes of illustration, but that various modifications may be made without deviating from the technology. For example, in some embodiments the high frequency SCS system can have 16 electrodes which are divided into four groups, with four electrodes in each group, for example. Each group can be stimulated for 25% of the time. In other words, each group of four electrodes is activated at a duty cycle of 25%. It should be understood that other suitable groupings of electrodes and other suitable duty cycles may be used in a similar fashion. Individual electrodes or electrode can have dedicated current sources, or all electrodes can be powered by a single current source, depending on the particular embodiment, which in turn can depend on parameters including, but not limited to, impedance values.

Certain aspects of the disclosure described in the context of particular embodiments may be combined or eliminated in other embodiments. Therapies directed to particular indications may be combined in still further embodiments. Additional indicators are disclosed in pending U.S. application Ser. No. 13/607,617, entitled "SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS," filed on Sep. 7, 2012, and incorporated herein by reference in its entirety. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

We claim:

1. A method of identifying patient responders to a paresthesia-free spinal cord stimulation therapy, the method comprising:
implanting in a patient a pair of spinal cord signal delivery devices, each having at least eight electrical contacts;
connecting an external signal generator to the spinal cord signal delivery devices;
initially simultaneously activating at least twelve of the electrical contacts with a therapy signal from the external signal generator without causing paresthesia in the patient while delivering the therapy;
implanting a signal generator in the patient if the patient responds favorably to the simultaneous activation of the at least twelve electrical contacts; and
after implanting the signal generator, applying the therapy signal to the patient via fewer than the at least twelve electrical contacts.

2. The method of claim 1, wherein at least a portion of the therapy signal is at a frequency in a frequency range between 1.5 kHz and 100 kHz.

3. The method of claim 2, wherein the amplitude of the therapy signal is between 0.5 mA and 20 mA.

4. The method of claim 1, wherein after implanting the signal generator, the therapy signal is applied via two of the plurality of electrical contacts.

5. The method of claim 1, wherein after implanting the signal generator, the therapy signal is applied at a duty cycle of less than about 17%.

6. The method of claim 1, wherein after implanting the signal generator, the therapy signal is applied at a duty cycle of less than about 10%.

7. The method of claim 1, further comprising monitoring the impedance of each of the fewer than the at least twelve electrical contacts and grouping the fewer than the at least twelve electrical contacts into a first group and a second group based on the impedance of the individual contacts and simultaneously activating the contacts of the first group of contacts using a first current source and the contacts of the second group of contacts using a second current source.

8. The method of claim 7, further comprising removing a selected contact from the first group if the selected contact's impedance is outside a selected range and including the selected contact in the second group.

9. The method of claim 1, further comprising simultaneously activating the at least twelve of the electrical contacts for a duration of approximately 20 minutes or more.

10. A method for deploying a patient therapy system, comprising:
implanting in a patient at least one spinal cord signal delivery device having at least 8 electrical contacts;
connecting an external signal generator to the at least one spinal cord signal delivery device;
determining whether the patient responds favorably to a paresthesia-free therapy signal from the external signal generator by initially simultaneously applying the signal to at least 75% of any of the electrical contacts;
implanting a signal generator into the patient when the patient responds favorably; and
after implanting the signal generator, applying the paresthesia-free therapy signal to a plurality of the electrical contacts fewer than the at least 75% of the electrical contacts via the implanted signal generator.

11. The method of claim 10, wherein at least a portion of the therapy signal is at a frequency in a frequency range from about 1.5 kHz to about 100 kHz.

12. The method of claim 10, wherein the therapy signal is at a frequency in a frequency range from about 3 kHz to about 50 kHz.

13. The method of claim 12, wherein the therapy signal is at a frequency in a frequency range from about 5 kHz to about 15 kHz.

14. The method of claim 10, wherein the therapy signal has an amplitude of less than 2.5 mA.

15. The method of claim 10, wherein the at least 75% of the electrical contacts includes twelve electrical contacts.

16. The method of claim 15, wherein the at least 75% of the electrical contacts includes all of the electrical contacts.

17. The method of claim 10, further comprising two spinal cord signal delivery devices, each having multiple electrical contacts.

18. The method of claim 10, further comprising monitoring the impedance of each of the fewer than the at least 75% of electrical contacts and grouping the fewer than the at least 75% of electrical contacts into a first group and a second group based on the impedance of the individual contacts and simultaneously activating the contacts of the first group of contacts using a first current source and the contacts of the second group of contacts using a second current source.

19. The method of claim 18, further comprising removing a selected contact from the first group if the selected contact's impedance is outside a selected range and including the selected contact in the second group.

20. The method of claim 10, further comprising simultaneously applying the signal to the at least 75% of the electrical contacts for a duration of approximately 20 minutes or more.

* * * * *

UNITED STATES PATENT AND TRADEMARK OFFICE
CERTIFICATE OF CORRECTION

PATENT NO. : 9,895,538 B1  
APPLICATION NO. : 14/161592  
DATED : February 20, 2018  
INVENTOR(S) : James R. Thacker et al.

Page 1 of 1

It is certified that error appears in the above-identified patent and that said Letters Patent is hereby corrected as shown below:

In the Claims

In Column 17, Line 16, Line 12 in Claim 1, delete "if" and insert -- when --, therefor.

Signed and Sealed this  
First Day of January, 2019

Andrei Iancu  
*Director of the United States Patent and Trademark Office*